(12) United States Patent
Krattiger (10) Patent No.: US 8,262,559 B2
(45) Date of Patent: Sep. 11, 2012

(54) APPARATUS AND METHOD FOR ENDOSCOPIC 3D DATA COLLECTION

(75) Inventor: Beat Krattiger, Beringen (CH)

(73) Assignee: Storz Endoskop Produktions GmbH (DE)

( * ) Notice: Subject to any disclaimer, the term of this patent is extended or adjusted under 35 U.S.C. 154(b) by 598 days.

(21) Appl. No.: 12/421,290

(22) Filed: Apr. 9, 2009

(65) Prior Publication Data

US 2009/0259098 A1 Oct. 15, 2009

(30) Foreign Application Priority Data

Apr. 11, 2008 (DE) .......................... 10 2008 018 636
Apr. 3, 2009 (EP) ..................................... 09004958

(51) Int. Cl.
 A61B 1/04 (2006.01)
 A61B 5/103 (2006.01)
 A61B 5/00 (2006.01)
(52) U.S. Cl. ......... 600/109; 600/590; 600/306; 600/117
(58) Field of Classification Search .................. 600/109, 600/590, 306, 117, 178, 182, 436, 475, 318; 356/5.1, 453, 456, 369, 402, 450; 328/255; 348/345, 349, 229.1
See application file for complete search history.

(56) References Cited

U.S. PATENT DOCUMENTS

| | | | |
|---|---|---|---|
| 4,998,971 A | 3/1991 | Fukunishi | |
| 5,534,992 A * | 7/1996 | Takeshima et al. | 356/5.1 |
| 5,693,003 A * | 12/1997 | Wolfelschneider et al. | 600/117 |
| 5,716,324 A * | 2/1998 | Toida | 600/160 |
| 6,293,911 B1 | 9/2001 | Imaizumi et al. | |
| 6,563,105 B2 | 5/2003 | Seibel et al. | |
| 2002/0040971 A1* | 4/2002 | Ono | 250/559.38 |
| 2002/0139920 A1* | 10/2002 | Seibel et al. | 250/208.1 |
| 2006/0025692 A1 | 2/2006 | Ishihara | |
| 2006/0034003 A1* | 2/2006 | Zalevsky | 359/738 |
| 2006/0052710 A1 | 3/2006 | Miura et al. | |

(Continued)

FOREIGN PATENT DOCUMENTS

DE 42 41 938 A1 6/1994

(Continued)

OTHER PUBLICATIONS

European Search Report; EP 09 00 4958; Jul. 15, 2009; 2 pages.

*Primary Examiner* — John P Leubecker
*Assistant Examiner* — Ronald D Colque
(74) *Attorney, Agent, or Firm* — St. Onge Steward Johnston & Reens LLC (57) ABSTRACT

An endoscopic apparatus includes a light-generating mechanism for generating at least one modulated measuring beam, a light-transmitting mechanism for conducting the measuring beam onto an area to be observed, where the light-transmitting mechanism includes an illuminating lens, in addition to a light-imaging mechanism for imaging a signal beam from the area to be observed at least onto a phase-sensitive image sensor, which includes a number of pixels, where the light-imaging mechanism includes an imaging lens. At least one additional image sensor is provided and the light-imaging mechanism includes a beam-splitter and/or an optical switch, where at least one adaptive lens is provided for adapting the fields of vision of the image sensors. As a result, an apparatus is created for endoscopic 3D data collection that is suitable for various types of image sensors.

14 Claims, 5 Drawing Sheets

U.S. PATENT DOCUMENTS

| | | |
|---|---|---|
| 2006/0055942 A1 | 3/2006 | Krattiger |
| 2007/0115551 A1* | 5/2007 | Spilman et al. ............... 359/494 |
| 2007/0149858 A1 | 6/2007 | Ogawa et al. |
| 2008/0009669 A1 | 1/2008 | Ozawa et al. |
| 2009/0040602 A1* | 2/2009 | Spilman et al. ............... 359/386 |

FOREIGN PATENT DOCUMENTS

| | | |
|---|---|---|
| DE | 9321266 U1 | 11/1996 |
| DE | 19840862 A1 | 3/2000 |
| DE | 10 2006 017 003 A1 | 10/2007 |
| EP | 0 434 793 B2 | 7/1991 |

* cited by examiner

APPARATUS AND METHOD FOR ENDOSCOPIC 3D DATA COLLECTION

CROSS-REFERENCE TO RELATED APPLICATIONS

The present application claims priority of European patent application No. 09 00 4958 filed on Apr. 3, 2009 and German patent application No. 10 2008 018 636.8-51 filed on Apr. 11, 2008.

FIELD OF THE INVENTION

The present invention relates to an apparatus for endoscopic 3D data collection as well as a related method.

BACKGROUND OF THE INVENTION

Apparatuses and methods for endoscopic 3D data collection are known in the art. For instance, U.S. 20060055942 A1 discloses a method for endoscopic distance measuring that is based on parallax shift of projected measuring points onto the observed object. Methods of this type are relatively robust, but the precision depends decisively on the triangulation base, which is always closely limited in endoscopic applications. In addition, these methods must make do with relatively few data points.

Patent DE 10 2006 017 003 A1 discloses an endoscope for depth acquisition in which a modulated light signal is emitted and the modulation parameters of the received light signal are used for computing the depth data. Two image sensors can receive radiation by means of a plane half-permeable mirror used as a beam splitter, where one of said sensors picks up the modulation parameters that can be used to produce 3D data, while the other mirror is provided to receive a visual image of the endoscopic scene.

It is often desirable to be able also to employ other types of image sensors, for instance to receive IR or spectrally sectioned or dissolved images and to depict or evaluate them together with the 3D data. Various types of image sensors, however, frequently have various formats or image diagonals. In the arrangement described in DE 10 2006 017 003 A1, then, only the image field of the smallest sensor can be used completely. If the image sensor with the smallest active surface is completely used, then with an image sensor having a greater surface, only part of the surface remains unused.

SUMMARY OF THE INVENTION

It is therefore the object of the present invention to produce an apparatus and a method for endoscopic 3D data collection in which the active surfaces of image sensors, even those having various sizes, formats, and/or lateral ratios, can be optimally used.

This object is realized by an apparatus having the characteristics set forth in the independent claims.

Because at least one adaptive lens system is provided for adapting the visual fields of the image sensors, the active surfaces of the image sensors can also be used optimally if said surfaces are of various sizes or comprise different lateral ratios.

Continual modulation of the measuring beam can be produced with relatively simple electronic means, and phase-sensitive solid body sensors are available that are of simple construction, easy to operate, and reasonably priced. Time delays, which correspond to differences in depth in the mm range of more than several meters, can be easily and reliably demonstrated with a corresponding frequency modulation. It is the pixel-triggered collection and evaluation of the phase information that makes possible the production of an image that depicts locally triggered depth and distance information. Thanks to the addition of the image of any desired additional image sensor, even one with different format, it is possible to have a simple and secure orientation in the 3D image as well as to obtain additional information, such as spectrally selected or triggered data.

An apparatus as in this invention includes light-generated means for producing at least one modulated measuring beam. The measuring beam can be generated in particular by employing light-emitting diodes (LEDs), superluminescent diodes, lasers, especially laser diodes or supercontinuum lasers, or other radiation sources that can be modulated accordingly. Laser diodes here have the particular advantage of simple handling and are economically priced, compact, and easily modulated. As a rule, multimodal laser diodes have the advantage of a higher output capacity than monomodal laser diodes.

The measuring beam here can be modulatable in sinus shape, possibly over a ground line. For better handling and more effective cooling, the light-emitting sources can be positioned in a separate housing, for instance as a separate light source.

In addition, an inventive apparatus comprises light transmission means for transmitting the measuring beam onto an area that is to be observed. The light transmitting means here can include, in particular, means for coupling the beam generated from the light source into a light conductor, as well as light conductors for transmitting the beam onward. Thus, for instance, a lens and/or mirror arrangement can be provided for improved coupling of the generated beam, or fiber-coupled superluminescent or laser diodes can be used. According to the invention, the coupling can proceed with a numerical aperture up to more than 0.25, making possible the use of a number of common superluminescent diodes or laser diodes. If the light-generating means are positioned in a separate housing or as a separate light source, then a light conductor cable, in particular, can be provided for transmitting the beam onward, said cable being provided with connecting means for linking with the light source or other light conductors.

At least one endoscopically applicable lighting optic is also provided. Such a lighting optic can be flexible, semi-rigid, or rigid and can consist of a light conductor fiber, a bundle of light conductor fibers, a light conductor rod, or another device for conducting light that can be inserted into a hollow space of an object or of a human or animal body. The light conductor fibers, in particular, can be multimode fibers. Means for distribution of the beam onto the area to be observed can also be provided, such as a diffuser or enlarging optic for uniform illumination of the object field, in particular at the distal (objective) end of the lighting optic. In particular when the beam is coupled or transmitted onward with a high numeric aperture, the enlarging optic can be completely or partly dispensed with.

To avoid coupling of undesired radiation, especially for reducing the heat impact in an endoscopic application in a living body, filtering means can also be provided, which filter out particular part of the produced radiation wholly or partly. Such filtering means can also be advantageous, for instance, in order to prevent undesired radiation from being received by an image sensor and to prevent its function or the validity of the image it produces from being adversely affected.

The inventive apparatus further includes light imaging means for imaging a signal beam from the area to be observed at least onto a phase-sensitive image sensor, so that the light imaging means include at least one imaging optic that is flexible, semi-rigid, or rigid and can be applied endoscopically. For said purpose, in particular, a lens arrangement, for instance an endoscope objective lens, can be provided. Said objective lens can produce an imaging onto an image sensor situated close to the distal end of the imaging optic. Image enlarging means can also be provided, for instance a rod lens system or an image conductor consisting of light conductor fibers, to conduct the image generated from the endoscope objective lens to the proximal (distant from the object) end of the imaging optic, where the imaging is conveyed onto an image sensor. The light imaging means can also include filtering means in order to block off certain parts of the received beam.

The illumination optic and the imaging optic are positioned in a shaft (29) that can be applied endoscopically and that can be rigid, semi-rigid, or flexible. The shaft, in familiar manner, can be inserted through a natural or artificial bodily opening into an inner bodily cavity or else, for instance, through an inspection opening into the interior of a technical component. In this case it can be advantageous, for reasons of handling, if the light-producing means are connected with the shaft as one compact unit. For this purpose, light-producing means with low loss capacity and small size are particularly appropriate, for instance superluminescent diodes or laser diodes.

In addition, the inventive apparatus includes control means for controlling the light-producing means and for powering the phase-sensitive image sensor, which is configured as phase-sensitive-powered firm body sensor. In particular, the control means permit the production of the modulation of the measuring beam and a corresponding powering of the phase-sensitive image sensor for the phase-selective reception of the received beam and for reading the signal of the phase-sensitive image sensor.

Finally, according to the invention evaluating means are provided to evaluate the data supplied by the phase-sensitive image sensor, which comprises a number of pixels, said data containing pixel-by-pixel phase information related to the modulation of the signal beam, to produce 3D data. Thus it is possible to draw conclusions from the phase information about the time delay between the emergence of the signal beam and the emission of the measuring beam, in order to produce an image that, for instance, depicts pixel-by-pixel this time delay and thus the running time to the observed object and back. Such an image, finally, can be depicted, for instance, on a video screen or else with the help of 3D representations.

According to the invention, at least one additional image sensor is provided so that the light imaging means include a beam splitter and/or an optical switch for imaging the beam returning from the object to the image sensors. The other image sensors can be configured, for instance, as CCD or as other semiconductor-image sensors, such as UV, IR, residual light, or other phase-sensitive image sensors.

The use of other sensors makes it possible to obtain additional information from an observed area, such as spectral or intensity information, or else information on a fluorescent image. Thereby it becomes possible, for instance in a diagnostic application, to recognize structures that do not emerge, or not clearly enough, in the visual image alone.

According to the invention a beam splitter is provided. Said beam splitter serves to divide the received beam into various observation radiation steps or sensors. One or more semipermeable mirrors, for instance, can be used as beam splitters, preferably in the form of partially reflected surfaces in image-splitting prisms or image-splitting cubes, so that the semipermeable mirrors can also be configured as dichroitic mirrors for spectrally selective image splitting. The use of semipermeable mirrors has the advantage that at every moment it is possible to gain information on various observation beam steps.

Alternatively or in addition to the foregoing, means for switching between various observation radiation steps or sensors can also be provided. These can be mechanical means, for instance a chopper, or else electrical means, such as an electrically powered mirror. The switching means can also be powered synchronously with the light producing means and/or with the phase-sensitive image sensor. Switching advantageously allows the alternating use of the various observation radiation steps.

In addition, an adaptive lens is provided to adjust the visual field of the phase-sensitive image sensor and of at least one additional image sensor. If, on theoretical grounds or from considerations of space or cost, use is made of image sensors that comprise different formats, this has the advantage that in some cases different sensor sizes or image diagonals and/or sensor formats do not result in fields of vision of different sizes, but rather the different image data in each case represent the same area. This is especially advantageous if a simple visual comparison of the different image data is intended to be possible by a user and if the comparison is not meant to be restricted to the smallest image field of the different sensors.

The adaptive lens is positioned between the beam splitter and at least one image sensor and thus can consist of one optic member or more and can, in particular, contain lenses with negative and/or positive refractive power or corresponding non-planar mirror elements including the semi-permeable mirror of the beam splitter. Consequently the image generated on an image sensor can be enlarged or reduced so that it images approximately the same visual field as on one or more other image sensors. To adjust to various formats or lateral ratios of the image sensors, the adaptive lens can also contain astigmatic optical elements. The adaptive lens can also be configured together with an image splitting prism or cube as a compact block. An enlargement adaptive lens can also make possible a reduction of the beam splitter and thus a reduction in weight, volume, and costs.

For setting, focusing, and/or adjustment, the adaptive lens can also be configured as variable, for instance as a zoom lens. This is especially advantage if the phase-sensitive image sensor and/or the at least one additional image sensor is configured as separable from the beam splitter or from an optical unit that includes the beam splitter. In this case, on applying an image sensor, a new setting for the image plane and/or enlargement can be required. In particular if an image sensor is replaced by a different type, the adjustment of the particular visual field can be made possible by an adjusting lens.

Consequently, the object of the invention is completely fulfilled.

In a preferred embodiment, at least the phase-sensitive image sensor is included in a video camera arrangement that is dissolubly connoted with the shaft that can be applied endoscopically. In particular, the video camera arrangement can be configured as a compact camera unit with a housing that, for instance, can be connected easily and securely with the endoscope shaft by means of an endoscope coupling.

According to another preferred embodiment, the illumination lens, the imaging lens, and the common shaft, which can be applied endoscopically, can be parts of a standard endoscope which can be a rigid, semi-rigid, or flexible endoscope. Such a standard endoscope can comprise an eyepiece for a direct view or else can be prepared for connection of a video camera unit by means of a C-mount.

This has the advantage that available endoscopes according to the invention can be used for the 3D data collection. Such endoscopes are available in a number of embodiments for various human and veterinary medical or technical applications. It is also possible to provide other components that are firmly or dissolubly connected with it in the distal area, such as beam splitters, image sensors, and so on, which are specific for 3D data collection. In this case the use of the other components of a standard endoscope makes possible at least an economical production, especially by using materials of proven environmental compatibility, sterilizability, heat-resistance, and so on.

In an additional configuration of the invention at least the adaptive lens, the phase-sensitive image sensor, at least one additional image sensor, and at least one adaptive lens inside the shaft that can be applied endoscopically are positioned close to its distal end. In addition, the illumination lens, close to the distal end, as well as other optical and electronic components can be included inside the shaft. This has the advantage that only electrical and/or light conductor cables must produce the connection between distal and proximal ends of the shaft, allowing the shaft to be of especially simple, economical, and slender construction, especially a flexible shaft.

In another preferred elaboration of the invention, at least the aforementioned components, and advantageously also other optical and electronic components, are combined to form a unit that is separable from the remaining part of the shaft and of the endoscope in the manner of a replaceable lens. This has the additional advantage that it is possible to use the endoscope also for other types of application than for fluorescence image formation.

Illumination means of various coherence can be used to generate the measuring beam. Upon illumination with a beam of high coherence the resulting image can be impaired with speckles. Said speckles generate apparent structures in the illumination strength and/or in the observed signal, which can cover up the structures of the observed object. According to a preferred embodiment of the invention, means for reducing the coherence are therefore provided in order to generate a uniform image. Thus the illumination means are powered in such a way, for instance, that the degree of coherence remains below a given threshold or, when speckles emerge in the generated image in considerable size, the degree of coherence is reduced. This can occur for instance with a laser diode by operation on or closely below the laser threshold, but it is also possible to power or modulate the laser diode in such a way that the coherence of the resulting beam is reduced.

In an inventive apparatus for 3D data collection, an eyepiece can also be provided. The direct view through an eyepiece has the advantage that, even independently of the image generation, an observation of the area to be observed is possible by image sensors in order, for instance, to make it possible for the user to have a simple orientation in a bodily cavity or in a technical component.

According to another preferred embodiment of the invention, an image sensor is provided which is configured for generating an image of the observed area by means of the reflected or scattered light. Such an image has the advantage that, for instance in a diagnostic application, it transmits the customary view of the tissue area that is to be diagnosed and consequently facilitates orientation. To distinguish between reflected and scattered light, polarization-optic elements can also be provided.

According to another preferred embodiment of the invention, a spectrally triggered or selected image of the observed area can be generated. For this purpose filters, for instance, can be provided that allow only a certain spectral portion of the reflected or scattered light to pass. An image that is spectrally divided into several portions, or selected according to a spectral portion, allows a high contrast in its representation and thereby improves the security of a diagnosis.

In the case of a narrow-band spectrally selective imaging, in particular, a spectrally selective element such as a prism or raster can be provided. The observed area is then imaged by point or line scans. As a result, a particularly high-contrasting image can be produced.

According to another preferred embodiment, an image sensor is provided for generating a fluorescent image. The additional image sensor can, in particular, in ways known in the art, be configured as an image sensor for a PDD system. The generated PDD image here can also contain part of the reflected or scattered light. The fluorescent image can also be a fluorescent lifelong image, which can also be corrected with the help of the 3D data in relation to the distance of the fluorescent surface.

The fluorescent image is available as a supplemental depiction of the observed area. As a result it becomes possible, for instance, to measure diseased modifications in a biological tissue with greater certainty.

According to another preferred embodiment the 3D data can be evaluated for measuring by length, area, or volume. With the assistance of distance information, the lateral extension of a structure can be ascertained from a 2D image of the observed area, and likewise the depth extension of the structure can be ascertained from distance data. In this manner it becomes possible to measure areas and to some extent volumes as well. This is especially advantageous in endoscopic applications where depth information necessary for ascertaining the imaging dimensions is not immediately available. Both in inspecting technical components and in medical diagnosis of tissue modifications, such measuring are desirable to determine the size and, in several dimensions, the modification over time of structures such as splits in technical components or lesions or tumors in human or animal organs. The measuring of areas or volumes can be combined with a fluorescent image in especially advantageous manner.

In another preferred embodiment of the invention, a stereo image is synthesized from the 3D data. Such a stereo image can be depicted for the viewer with an appropriate display device, which displays different images for each of the viewer's eyes, and provides the viewer with a spatial impression of the observed area that is close to reality. This is particularly desirable with endoscopic procedures for improving haptics, that is, the operator's intuitive control of the instruments he or she uses. Because the synthetic stereo base can be selected with virtually complete freedom of choice and is restricted only by the need to avoid overlapping, the stereo effect here can be adapted to any desired endoscopic procedural situations, even for instance for robot-supported procedures. The mechanical translation ratios of the manipulators, the optical imaging dimensions, and the stereo effects can be selected in such a way that they are adapted to one another.

To compute the left or right stereo image, on the basis of a 2D image, for instance a color or gray-scale image, in the left image all pixels are individually displaced to the right by a factor that is approximately inversely proportional to the distance that was ascertained with the 3D sensor. In the right image, accordingly, all pixels are displaced to the left. If necessary it is possible also o make a pixel smoothing and a correction of the distortion. These image-processing operations can also be carried out in real time on the running video image. The two images can then be depicted, for instance, on a stereo image screen or with a stereo viewing device.

The inventive apparatus, according to a particularly preferred embodiment, can be configured in such a way that the image data furnished by the phase-sensitive image sensor and at least one additional image sensor, or also by the image data furnished by a video camera connected to the eyepiece, can be depicted in a synoptic manner. Such a depiction can be a layered depiction of the particular image data, an alternating depiction, or one depiction after another, or a grouping of images side-by-side with one another. To provide a depiction for one user, suitable display devices can be provided such as one or more video screens, projectors, printers, and so on. Storage means can also be provided for recording, documenting, and archiving image data. The control and evaluation means, in addition, can be configured for conducting image analysis procedures, which can be selected independently of the user or by the user. As a result, contrasts, for instance, can be accentuated or reduced, data can be smoothed, or structures from the image data generated from various image sensors can be correlated with one another. Thus, for instance, information from a visual or X-ray image, from AF or PDD images and/or a fluorescent image can be combined with the 3D data or with one another.

The control and evaluation device can also be configured, by correlation of the image data of the various image sensors, to produce automatically a precise layering of the image data or else to carry out an automatic adaptation of the visual fields concerning position, size, and/or format. Likewise, possibly depending on the sensor, an automatic focusing or an automatic correction of distortion can be provided.

According to another preferred embodiment of the invention, means are provided not only to generate light that is suited as a measuring beam and to transmit it onward to the area to be observed, but also at least one additional beam. This could be white light, for instance, for generating a white light image during observation through an eyepiece or by means of a related additional image sensor. For this purpose corresponding light-generating means can be provided, for instance a xenon or metal-halide light, for generating a white light illumination, which can be positioned in a light source of its own or in a common light source together with the light-generating means for the measuring beam.

Likewise, to generate a broadband illumination, fiber-pumped fluorescent light sources, such as is disclosed for instance in US 20070092184 A1, can be used, if they comprise sufficiently brief fluorescent lifetime. Using supercontinuum white light laser sources has the additional advantage that they can be modulated, possibly synchronously with the phase-sensitive image sensor. In addition, supercontinuum white light lasers can radiate wavelength-selectively and accordingly can be powered electrically. Such a light source can suffice for generating all necessary types of beam.

The measuring beam itself can often be used for generating an image in reflected or scattered light. However, a broadband, especially a white light, illumination can be used advantageously for generating such an image, for instance through a xenon light source.

The additional beam can be generated simultaneously with the measuring beam and can be transmitted onward in the area to be observed, or else it can be generated or transmitted onward in alteration with the measuring beam through corresponding powering and/or through an optical switch element. The latter is especially advantageous if an illumination with the particular beams is not necessary at all times, and at other times the beam that is not required can be switched or blocked off in order to reduce the connected energy quantity. The switch frequency can be set high enough that the switching is no longer detectable, or only slightly so, with the eye or on the display device. In particular, the alternating frequency can be synchronized with the image frequency in such a way that an entire number of video images fall within half of an alternating period.

An inventive method for endoscopic 3D data collection includes the following steps:
generation of at least one modulated measuring beam,
transmitting the measuring beam forward to an area to be observed by means of at least one illuminating lens that can be applied endoscopically,
imaging of a signal beam from the area to be observed at least onto one phase-sensitive image sensor, which comprises a number of pixels, by at least one imaging lens that can be applied endoscopically,
where the illuminating lens and the imaging lens are positioned in a shaft that can be applied endoscopically, and generation of 3D data by evaluation of the data delivered by the phase-sensitive image sensor,
where at least one additional image sensor and one beam splitter and/or an optical switch are provided, and
at least one adaptive lens is provided for adapting the visual fields of the image sensors.

It is understood that the aforementioned characteristics and those yet to be disclosed can be used not just in the individually indicated combination but also in other combinations or in isolation, with departing from the framework of the present invention.

BRIEF DESCRIPTION OF THE DRAWINGS

Further aspects of the invention can be seen from the following description of a preferred embodiment and the appended illustrations.

DETAILED DESCRIPTION OF THE INVENTION

Figure 1:
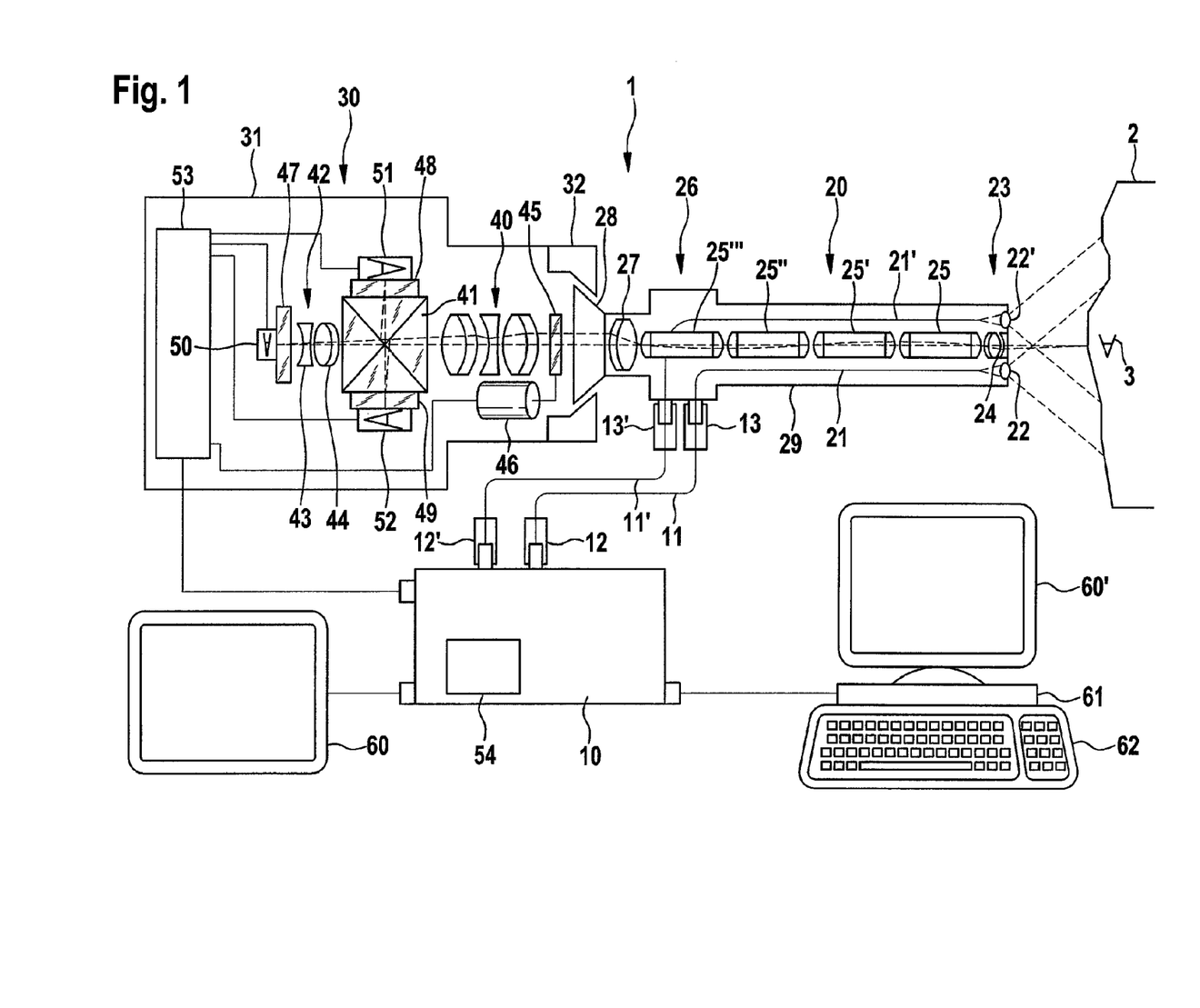
FIG. 1 shows a preferred embodiment of an inventive apparatus.

According to FIG. 1, an inventive apparatus 1 includes a light source 10. In the illustrated preferred embodiment, the light source is configured for generating a continuous, for instance sinus-shaped, modulated measuring beam and a white light illumination. For transmitting both types of beam onward, light conducting cables 11, 11' are provided respectively, and said cables can be connected by connections 12, 12' with the light source 10 and by connections 13, 13' with the endoscope 20. In a corresponding coupling or by using a supercontinuum laser, both types of beam can also be transmitted by a single light conductor. The light source can also be integrated in the endoscope.

The measuring beam and the white light are conducted to the end 23 close to the object (the end remote from the observer, or distal end) of the endoscope 20 by the endoscope light conductors 21, 21'. The enlarging lenses 22, 22' situated there serve to uniformly distribute the illuminating beam onto the area to be observed, for instance an object 2, such as an area of tissue in an internal bodily cavity (not illustrated).

To generate an image of a partial area of the object 2, the endoscope 20 comprises an endoscope objective lens 24. The intermediate image produced by it is conducted by a relay lens system, here an arrangement of rod lenses 25 25', 25", 25''', to the end 26 farther from the object (the end close to the observer, or proximal end) of the endoscope 20. If, instead of the illustrated rigid endoscope 20, a flexible endoscope is used, then the generated image can be transmitted by glass fiber image conductors. An eyepiece lens arrangement 27 is provided on the proximal end of the endoscope. As long as the video camera arrangement 30 is not affixed on the endoscope 20, a direct view is possible through the eyepiece cup 28. Here the endoscope light conductors 21, 21', the endoscope objective lens 24, and the relay lenses 25, 25', 25'', 25''' are included in an endoscope shaft 29 that can be inserted into a body cavity.

For 3D data collection, a video camera arrangement 30 can be affixed to the endoscope 20. Said arrangement contains in a housing 31 one or more optical sensors, as well as other optical and possibly electronic components. An endoscope coupling 32, provided for dissoluble connection with the endoscope 20, can include for instance a snapping or bayonet mechanism in order to ensure easy, secure, and dissoluble connection. In particular, an abutment surface (not illustrated) can be provided in order to fix the relative position of the endoscope and video camera arrangement, and a delivery window (not illustrated) can be provided to present soiling of the video camera arrangement.

The video camera arrangement contains a camera objective lens 40, a beam splitter configured as a partial cube 41 for splitting the image into several image sensors, image sensors 50, 51, 52, and an adaptive lens 42, depicted here by way of example with the image sensor 50. The adaptive lens 42 contains, for instance, a lens or group of lenses with negative refractive power 43, and a lens or group of lenses with positive refractive power 44, and is configured in such a way that the same image field is imaged on the active surface of the image sensor 50 as on the image sensors 51 and 52 despite different size. This is shown symbolically in FIG. 1 in the illustrated structure 3, which the adaptive lens configured as a reducing lens depicts as smaller on the smaller image sensor 50 than on image sensors 51 and 52.

In addition the video camera arrangement contains preparatory lenses 45, 47, 48, 49, which can in particular be configured as filters and/or as optical switches. The preparatory lenses can comprise, for instance, color filters, in particular absorption or interference filters, electronically adjustable filters, prisms, extension plates, or room frequency filters (anti-aliasing filters). Thus, in particular, the preparatory lens 45, which is upstream of all image sensors, can be determined for eliminating light portions that are undesired for all image sensors. An actuator 46 can be associated with the preparatory lens 45, for instance for rotating a filter inward or outward. The preparatory lenses 47, 48, 49 serve in particular to filter the arising light corresponding to the particular type of sensor.

Thus, for instance, the image sensor 50 can be configured as a phase-sensitive firm body image sensor, which pixel-by-pixel registers the intensity of the arising signal beam and the phase displacement, that is, the time delay between the measuring beam and arising signal beam. Three-dimensional data can be reconstructed from data supplied by this image sensor. The phase displacement and thus the time delay, corresponding to the signal running time, can be ascertained pixel-by-pixel by the corresponding evaluation, as indicated for instance in EP 1 746 410 A1.

The image sensor 51 in the embodiment produces a color X-ray image. The preparatory lens 48 can be configured for this purpose as an IR blocking filter for instance. The image sensor 52, for instance, can produce an image in the NIR range, but could also for instance assume a heat image or contain an image intensifier to increase sensitivity.

Preparatory lenses can also be configured as electronically controllable filters for instance as liquid crystal tunable filter (LCTF) or as acoustic-optical tunable filter, AOTF). The beam splitter can also be configured spectrally selectively, for instance by a dichroitic layer, so that a low portion of light is lost in blocking filters.

The image sensors 50, 51, 52 are connected with a control electronics 53, which controls the image sensors and reads the image data and, possibly after an initial preparation, transmits them onward. The control electronics 53 is also connected with the light source 10, so that the reading of data and the modulation of the measuring beam can be synchronized. In addition a control device 54 is provided which, for instance, can be integrated into the light source 10. In addition, display devices 60, 60' are provided for displaying image data, as well as a data entry unit, for instance a keyboard 62, a touch screen, or a language recognition device.

The control apparatus 54 processes the image signals for immediate display, controls the light source 10 synchronously with the image sensors, controls filters that can in some cases be powered, and conducts the image data onward to a computer 61 for further processing, display, and storage. In addition a means for linking or synoptically depicting the various image data, as well as, in some cases, the production of a synthetic stereo image, is provided in the control apparatus or in the computer 61.

Figure 2:
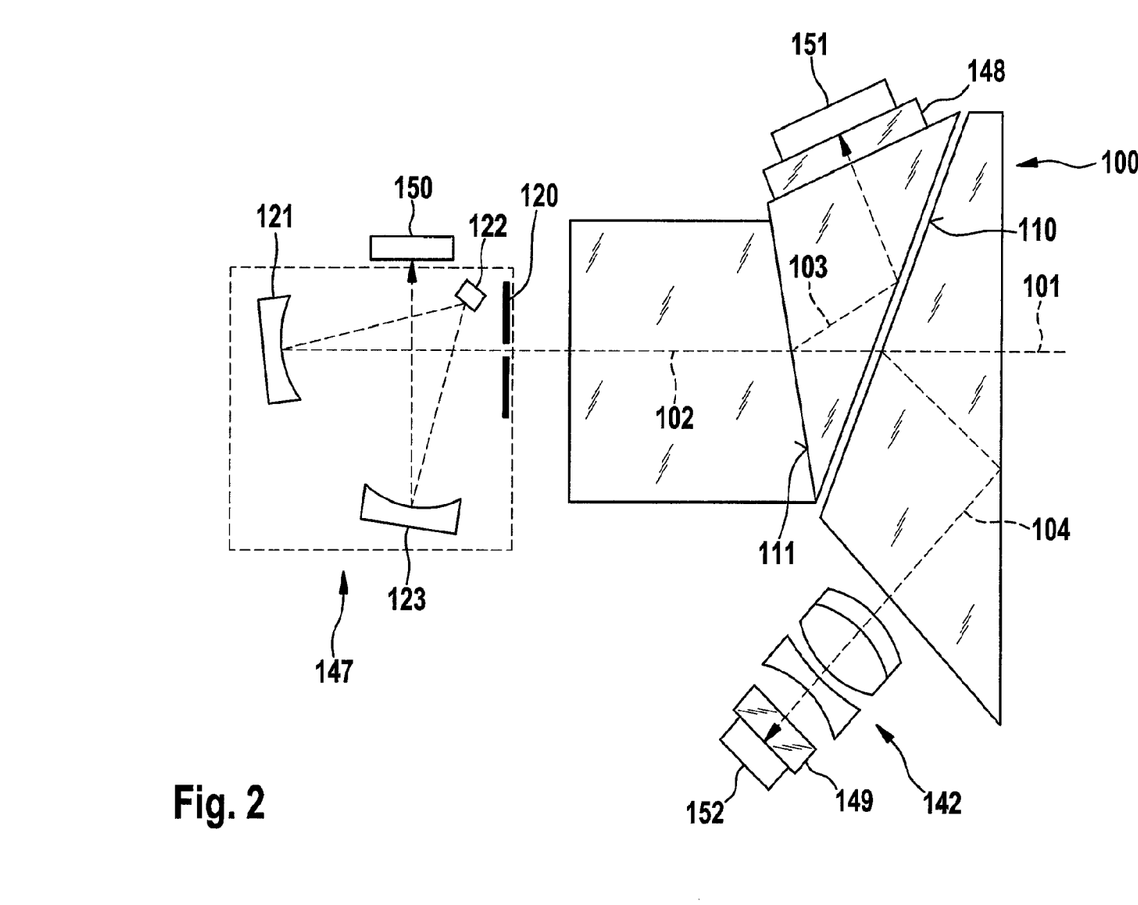
FIG. 2 shows an alternative embodiment of a beam splitter used in an inventive apparatus.

An alternative configuration of the beam splitter is shown in FIG. 2. Instead of the beam splitter cube 41, here prisms are provided for dividing the light, which form a prism block 100.

The incident beam 101 is broken up into two border surfaces 110 and 111 in a total of three channels 102, 103, and 104. These channels conduct the light onto three image sensors 150, 151, 152, of which at least one is a phase-sensitive image sensor. The incident intensity can be reflected into the individual channels with metallic coating in neutral color in predetermined intensity ratios, and can also be color-selectively or spectrally broken down with dichroitic coating. By introducing additional surfaces, more channels can also be produced, by a simple splitter prism even just two channels.

Here an adaptive lens 142 is provided before the image sensor 152, as well as a preparatory lens 149, for instance a filter. The preparatory lens before the image sensor 151 can also be a filter 148, for example. A crossed Czerny-Turner spectrometer 147 serves as preparatory and adaptive link before the image sensor 159 in this embodiment. The central image row is selected, for instance, by the line aperture 120, and a diffraction grating 122 or else a diffractive optical element or prism by the first hollow mirror 121, and illustrated on the image sensor 150 by the second hollow mirror 123. As a result, a spectrally dissolved image, dissolved spatially in one dimension, can be produced. A complete image can be assembled in mosaic fashion, in that the illustrated rows are conducted over the object, for instance by swiveling the endoscope back and forth, which can be done manually or mechanically by a corresponding swivel device, for instance in a swivel-view endoscope, or by automatic scanning by moving the line aperture 120 and/or the spectrometer 147.

For this purpose corresponding control and evaluation software is installed in the control device.

Figure 3:
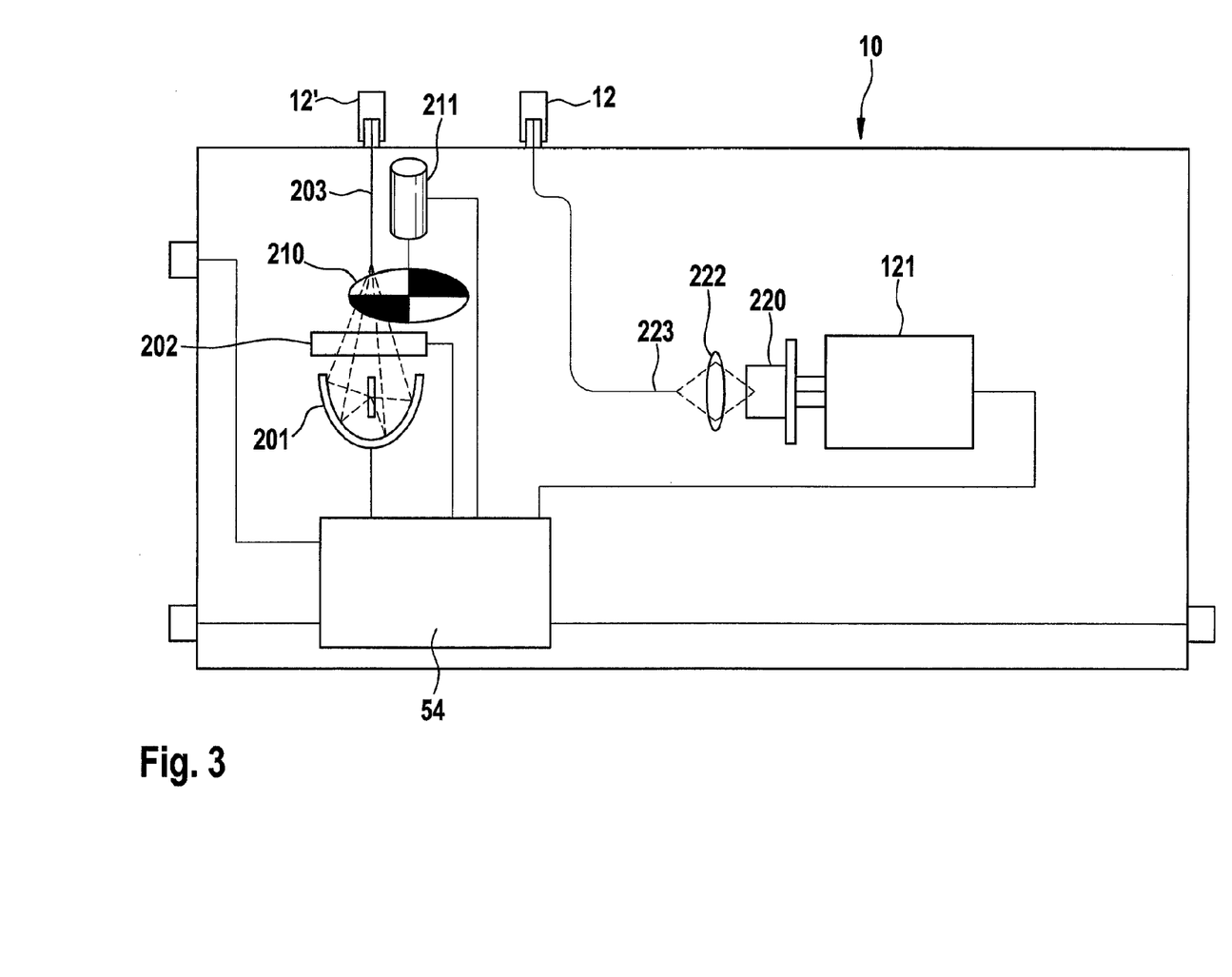
FIG. 3 shows an inventive light source.

As is shown in FIG. 3, according to the invention the light source 10 can contain the control device 54, which communicates with the control electronics 53, display devices such as a screen 60, and other apparatuses such as a computer 61 and for this purpose can be connected by plug-in connections. The control device also controls the light production, for instance of white light and measuring beam.

For this purpose the light source 10 contains as white light source a metal-halide-arc discharge lamp 201, which can include a reflector, as well as other elements for collimation or coupling in a light conductor 203. Alternatively, LED, xenon, or halogen lamps can be used as white light source, as well as x-ray or super continuum laser sources. To prevent white light from adversely affecting depth measuring, a chopper wheel 210 is provided, which interrupts the light flow as soon as a distance data collection occurs. This can be entered manually in order to make alternating observations in white light and in measuring light, or else to record a fluorescent image. It is also possible to switch between white light or fluorescent observation and 3D measuring in video beat or a fraction thereof. The control device controls the powering 211 of the chopper wheel corresponding to the particular requirements, for instance synchronously with the reading of the particular image sensor. Instead of a chopper wheel, an oscillating mirror or an electronically controlled filter can be used. When using firm body light sources, such as LED or laser light sources, these can be directly powered in the corresponding beat. The light conductor 203 feeds the light over a connection 12' into a light conductor cable.

To produce the measuring beam, a laser diode 220 is proved that is powered by a driver electronics 221 and whose light is coupled by a collimation lens 222 into a light conductor 223. Alternatively a fiber coupled light diode or a superluminescent diode can be employed. The generated light is fed by a connection 12 into a light conductor cable to be transmitted onward into the endoscope. The laser diode is modulated by the control apparatus synchronously with the reading of the phase-sensitive image sensor.

Figure 4:
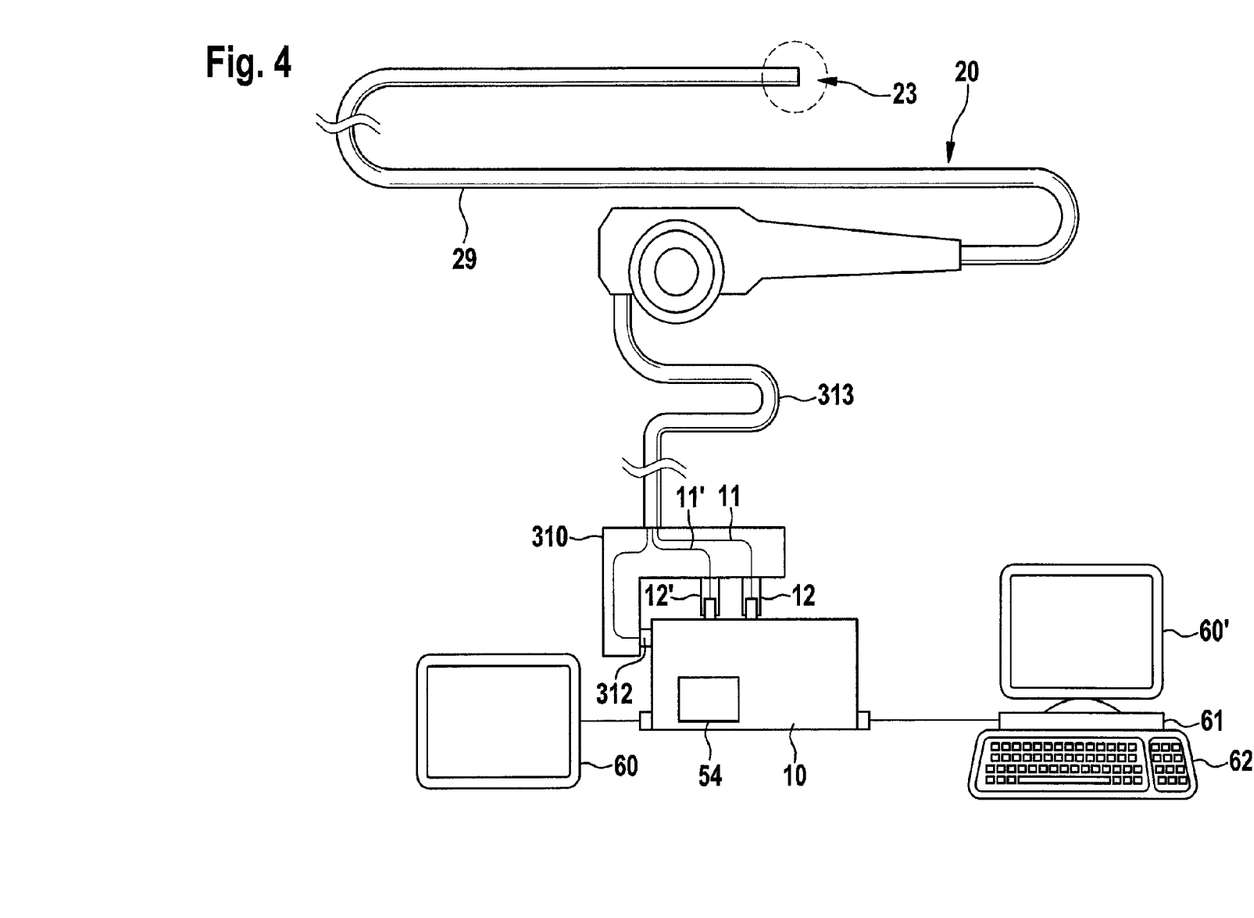
FIG. 4 shows an additional embodiment of an inventive apparatus.
Figure 5:
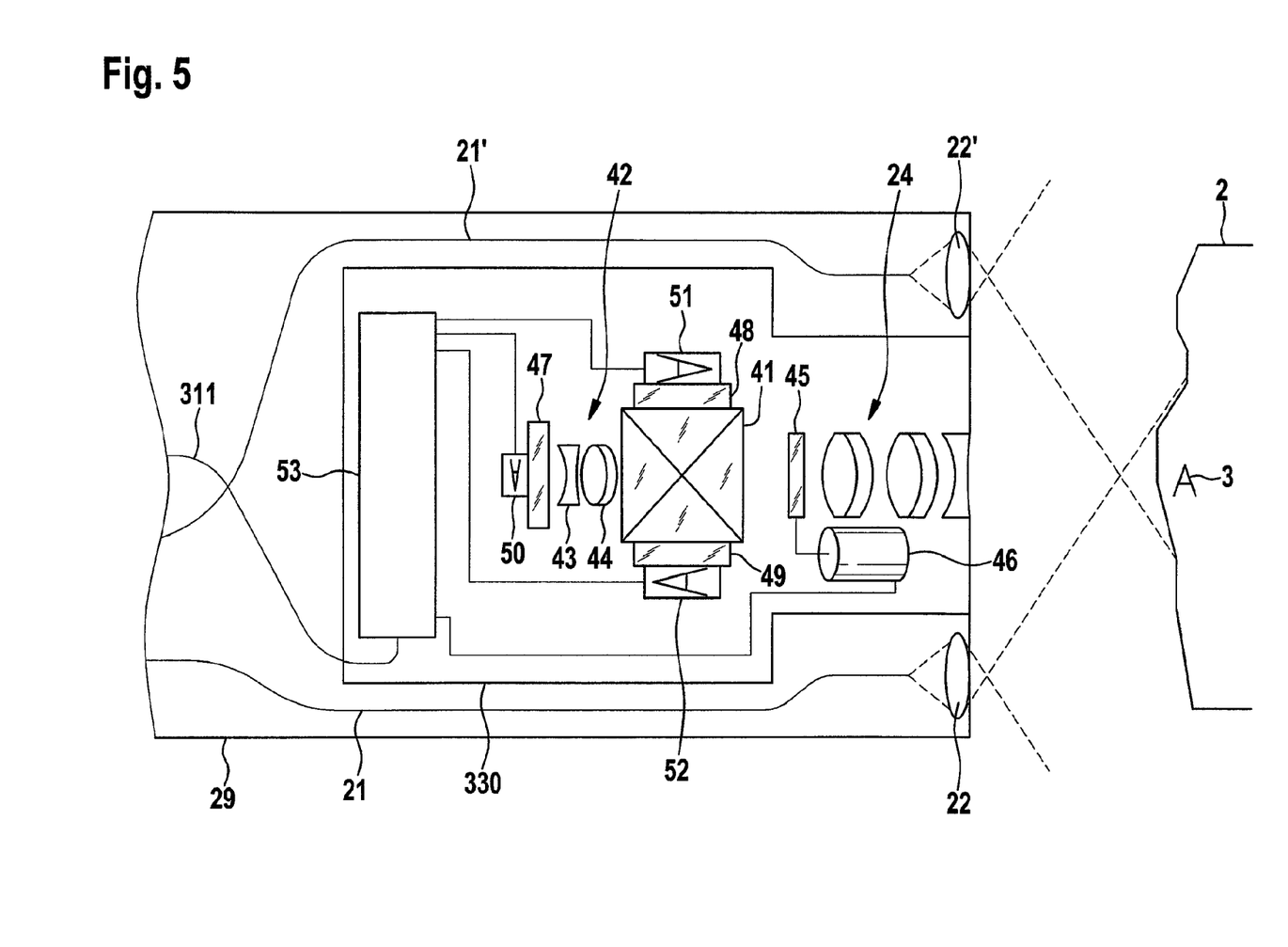
FIG. 5 shows an enlarged detail from FIG. 4.

In the additional embodiment of the invention shown in FIG. 4, the optical and electronic components, which are combined in the embodiment of the video camera arrangement 30 as shown in the FIG. 1 embodiment, are arranged inside the endoscope shaft 29 close to its distal end 23, which is depicted in detail in FIG. 5. Neither a relay lens system nor a glass fiber image conductor for transmitting the image generated from the endoscope objective lens to the proximal end of the endoscope nor an eyepiece is necessary here. The endoscope objective lens 24 here includes all the lenses in front of the beam splitter 41, and an additional video camera objective lens is not necessary. The preparatory lens 45, for instance a filter that can rotate inward, is positioned here for instance between the endoscope objective lens 24 and the beam splitter 41. The endoscope objective lens 24 and the components belonging to the video camera arrangement 30 can be combined to form a distal video camera unit 330, which can be dissolubly connected with the remaining part of the endoscope 20 by a coupling (not illustrated) and can be exchangeable with other video camera units in the manner of an exchangeable head or objective lens. The distal video camera unit 330 can also include the distal illuminating lens, in particular the enlarging lenses 22, 22', and parts of the endoscope light conductors 21, 21' associated with them, as well as the distal end of the endoscope shaft 29.

The endoscope shaft 29 in this embodiment is flexible but can also be semi-rigid or rigid. The control electronics 53 is connected with the control apparatus 54 by a cable 311, which, together with the light conductor cables 11, 11', leads through the endoscope shaft 29 and an endoscope cable 314. To connect the endoscope 20 with the light source 10 and with the control apparatus 54, the connections 12, 12' and the connection 312 of the cable 54 can be combined in a connector box 310.

The structure of the endoscope 20 corresponds advantageously to that of a standard videoscope. For the description of additional individual units, see FIG. 1.

If an inventive method for endoscopic 3D data collection is to be used, then the endoscope 20 is inserted into the body cavity or into the technical component in which the measuring is to take place. The video camera arrangement 30, if it does not form a unit with the endoscope or is not already connected with it, is connected to the endoscope 20, for instance clipped by the endoscope coupling 32 onto the eyepiece cup 28. If the light-generating means are not part of the endoscope, then the light source 10 is connected with the endoscope 20 by the light cables 11, 11'. The endoscope 20 is advantageously secured on a bracket which prevents any motion by the endoscope relative to the investigated object during the examination.

To apply the inventive method for 3D data collection, the illuminating light is generated in the light source 10, in particular the measuring beam and white light. The white light can embrace the entire visible range, for instance, or part of it, or else can consist of one or more narrow-band portions. The measuring beam is intensity-modulated in sinus form with a power of, for instance, approximately 10 to 100 MHz. The white light is advantageously switchable in the video beat.

White light and a measuring beam are conducted by the light cables 11, 11' and the light conductors 21, 21' onto the area to be observed. An image is generated by the imaging lens on the phase-sensitive image sensor 50. By means of a reading of the image sensor synchronized with the modulation of the measuring beam, phase-dependent data are obtained pixel by pixel, which are processed by the control electronics 53 and the control apparatus 54 to yield intensity and phase information. As a result, the control apparatus generates depth information, which depicts the time delay of the signal beam with respect to the measuring beam, and from there in turn 3D data. A fluorescent image can likewise by generated.

The 3D data can be depicted for the user on suitable display devices and remain available for further image processing steps or for storage. An x-ray or fluorescent image can be depicted for this purpose, for instance in alteration with or overlaid on the 3D data.

The invention claimed is:

1. An apparatus for endoscopic 3D data collection having:
light-generating means for generating at least one modulated measuring beam,
light-transmitting means for transmitting the measuring beam onward to an area to be observed, where the light-transmitting means includes an illuminating lens that can be applied endoscopically,
light-imaging means for imaging a signal beam from the area to be observed onto at least one phase-sensitive image sensor, which comprises a plurality of pixels, where the light-imaging means includes an imaging lens that can be applied endoscopically,
where the illuminating lens and the imaging lens are positioned in a shaft that can be applied endoscopically, and
control and evaluation means for controlling the light-generating means, for powering the phase-sensitive image sensor, and for evaluating data supplied by the phase-sensitive image sensor for generating 3D data,
where at least one additional image sensor is provided and the light-imaging means includes at least one of a beam-splitter and an optical switch, distinguished in that
the image sensors have different formats, and
at least one adaptive lens is provided for adapting fields of vision of the phase-sensitive image sensor and the additional image sensor.

2. The apparatus according to claim 1, wherein one camera arrangement is provided which contains at least the phase-sensitive image sensor and which is detachably connected with the shaft that can be applied endoscopically.

3. The apparatus according to claim 2, wherein the illuminating lens, the imaging lens, and the shaft that can be applied endoscopically are parts of a standard endoscope.

4. The apparatus according to claim 1, wherein at least the imaging lens, the phase-sensitive image sensor, at least one additional image sensor, and at least one adaptive lens are positioned close to a distal end of the apparatus.

5. The apparatus according to claim 1, wherein means are provided for coherence reduction.

6. The apparatus according to claim 1, wherein an image sensor is provided for generating an image by means of an at least one of reflected and scattered light.

7. The apparatus according to claim 6, wherein the image generated by means of the at least one of reflected and scattered light is spectrally dissolved or selected.

8. The device according to claim 7, wherein the spectrally dissolved or selected image is obtained through point or line scanning.

9. The apparatus according to claim 1, wherein an image sensor is provided for generating a fluorescent image.

10. The apparatus according to claim 1, wherein the 3D data can be evaluated for at least one of length, area, and volume measuring.

11. The apparatus according to claim 1, wherein a stereo image is synthesized from the 3D data.

12. The apparatus according to claim 1, wherein the control and evaluation means are configured to generate a synoptic depiction of data provided by the phase-sensitive image sensor and by at least one additional image sensor.

13. The apparatus according to claim 1, wherein the light-generating means is provided to generate at least one additional illuminating beam.

14. A method for endoscopic 3D data collection, comprising the following steps:
   generating of at least one modulated measuring beam,
   transmitting the measuring beam on to an area to be observed by means of at least one illuminating lens that can be applied endoscopically,
   imaging a signal beam from the area to be observed onto at least one phase-sensitive image sensor, which includes a plurality of pixels, by at least one imaging lens that can be applied endoscopically,
   where the illuminating lens and the imaging lens are situated in a shaft that can be applied endoscopically, and
   generating 3D data by evaluating data provided by the phase-sensitive image sensor,
   providing at least one additional image sensor and at least one of one beam splitter and one optic switch,
   characterized by
   the image sensors having different formats, and
   providing at least one adaptive lens for adapting the visual fields of the phase-sensitive image sensor and the additional image sensor.

* * * * *